United States Patent [19]

Buckler et al.

[11] Patent Number: 4,795,828
[45] Date of Patent: Jan. 3, 1989

[54] FUNCTIONALIZED INTERMEDIATE FOR THE SYNTHESIS OF ALPHA-FUNCTIONALIZED DERIVATIVES AND LABELED CONJUGATES OF PROCAIMAMIDE AND NAPA

[75] Inventors: Robert T. Buckler, Edwardsburg; Frederick E. Ward, Elkhart, both of Ill.

[73] Assignee: Miles Inc., Elkhart, Ind.

[21] Appl. No.: 911,524

[22] Filed: Sep. 25, 1986

Related U.S. Application Data

[62] Division of Ser. No. 713,041, Mar. 18, 1985, Pat. No. 4,673,763, which is a division of Ser. No. 455,223, Jan. 3, 1983, abandoned.

[51] Int. Cl.[4] .................... C07C 87/20; C07C 101/24
[52] U.S. Cl. ..................................... 564/512; 562/561
[58] Field of Search ..................... 564/512; 562/561

[56] References Cited

U.S. PATENT DOCUMENTS 3,031,490  4/1962  Ferris et al. ..................... 562/561
4,235,969  11/1980  Singh et al. ..................... 424/88

FOREIGN PATENT DOCUMENTS 0127098  12/1984  European Pat. Off. ............ 562/561

Primary Examiner—Glennon H. Hollrah
Assistant Examiner—John A. Sopp
Attorney, Agent, or Firm—Daniel W. Collins

[57] ABSTRACT

Procainamide and N-acetylprocainamide (NAPA) immunogens, antibodies prepared therefrom, labeled conjugates, synthetic intermediates, and the use of such antibodies and labeled conjugates in immunoassays for determining the respective drugs. The immunogens comprise the drugs coupled at the α-position of the amide side chain to an immunogenic carrier material. The labeled conjugates and synthetic intermediates similarly are α-position derivatives of the drugs or precursors thereof. The antibodies and labeled conjugates are particularly useful in homogeneous nonradioisotopic immunoassays for measuring the respective drugs in biological fluids such as serum.

3 Claims, 2 Drawing Sheets

FUNCTIONALIZED INTERMEDIATE FOR THE SYNTHESIS OF ALPHA-FUNCTIONALIZED DERIVATIVES AND LABELED CONJUGATES OF PROCAIMAMIDE AND NAPA

This is a division of application Ser. No. 713,041, filed Mar. 18, 1985, now U.S. Pat. No. 4,673,763, issued 6-16-87, which is a division of application Ser. No. 455,223, now abandoned.

BACKGROUND OF THE INVENTION

1. Field of the Invention

This invention relates to novel procainamide and N-acetylprocainamide (NAPA) derivatives pertaining to immunoassays for determining such drugs in liquid media such as biological fluids. The derivatives include immunogens used to stimulate production of antibodies to the drugs in host animals by conventional techniques. Also provided are labeled conjugates used as reagents, along with the antibodies, in particularly preferred immunoassays. Intermediates in the synthesis of the aforementioned immunogens and labeled conjugates are also provided.

The cardiac depressant drugs procainamide and N-acetylprocainamide are used clinically to treat or prevent cardiac arrhythmia (J. Kosh-Weser, et al, *New England J. Med.* 281: 1253 (1969); J. Koch-Weser and S. W. Klein, *J. Am. Med. Assoc.* 215: 1454 (1971)]. N-acetylprocainamide (abbreviated as NAPA and also known as acecainide) is the major metabolite of procainamide in man. The concentration of this metabolite in the plasma of patients receiving procainamide often exceeds the concentration of the parent drug itself. Metabolism is by in vivo acetylization and much genetic-based variation has been observed in the rate at which individual patients transform the drug to its metabolite [D. Drayer, et al, *Drug Metab. Rev.* 10: 239 (1979)]. This phenomenon is of importance in the clinical use of the drugs because of the lower incidence of side effects associated with NAPA. Both the therapeutic usefulness and the toxicity of the drugs are better correlated with their blood levels than with their dosages. The relationship between the amount of drug administered and the blood levels is quite variable. It is influenced by completeness of absorption, distribution characteristics and rates of metabolism and excretion.

2. Description of the Prior Art

Because of these considerations, numerous analytical methods have been developed to determine the blood levels of these drugs, including high pressure liquid chromatography (HPLC) [L. R. Shukus, et al, *Clin. Chem.* 23: 705 (1977)], homogeneous enzyme immunoassay [C. B. Walberg, "Proc. Intl. Sym. Enzyme Labeled Hormones and Drugs", S. B. Pal, ed., W. de Gruyter & Co. (Berlin, 1978), p. 429], and quantitative thin layer chromatography (TLC) [B. Wesley-Hadzya and A. M. Mattocks, *J. Chromat.* 143: 307 (1977)].

The preparation of antibodies to procainamide and NAPA for use in immunoassays to determine the drugs has been accomplished in the prior art by essentially two different approaches. One approach has been to couple procainamide through the ring amino group by diazotization subsequent condensation to an albumin carrier [A. S. Russel, et al, *Clin. Exp. Immunol.* 3: 901 (1968) and Mojaverian et al, *J. Pharm. Sci.* 69: 721 (1980)]. The resulting antibodies show a high degree of cross-reactivity with NAPA and would therefore be unsuited for use in immunoassays specific for one or the other drug.

The second approach involves coupling of the drugs at the complete opposite end of their structures, at the N-diethylamino group, by modification of one of the ethyl substituents for subsequent coupling to a carrier [U.S. Pat. No. 4,235,969]. As a result, antibodies are raised against an immunogen in which a major functional group of the drugs has been modified in order to couple them to the carrier.

The state-of-the-art of preparing antibodies to haptens such as drugs is represented by Weinryb et al, *Drug Metabolism Reviews* 10: 271 (1979); Playfair et al, *Br. Med. Bull.* 30: 24 (1974); Broughton et al, *Clin. Chem.* 22: 726 (1976); and Butler, *J. Immunol. Meth.* 7: 1 (1975) and *Pharmacol Rev.* 29(2): 103 (1978).

Labeled conjugates, comprising the analyte or a derivative or other analog thereof, coupled to a labeling substance are variously described in the literature, e.g., U.S. Pat. Nos. 4,279,992; 4,182,856; 4,259,233; and 4,292,425 wherein the label is the fluorogenic enzyme substrate $\beta$-galactosyl-umbelliferone.

SUMMARY OF THE INVENTION

The present invention uniquely provides reagents for use in procainamide and NAPA immunoassays involving the coupling to or derivatization of the drug at the $\alpha$-position on the amide side chain. The immunogen of the present invention, comprising the haptenic drug covalently linked at the $\alpha$-position to an immunogenic carrier material, stimulates the production of antibodies to the respective drugs. By coupling the drug at the $\alpha$-position where no substituents appear in the parent drugs, the immunogen conjugate is prepared without modifying any functional or distinguishing groups on the drugs.

In a preferred embodiment, the present invention provides novel intermediates in the preparation of the $\alpha$-substituted drug-carrier immunogens. Also provided are an improved immunoassay method and reagent means for the determination of the drugs with the use of the novel antibodies of the present invention. The present invention also provides labeled conjugates for particularly preferred embodiments of such immunoassay.

DESCRIPTION OF THE PREFERRED EMBODIMENTS

The present invention, in all of its interrelated embodiments, is focused on preparation of $\alpha$-substituted drug derivatives which can then be used to form immunogens by coupling them to conventional carrier materials, and subsequently used to obtain antibodies, or can be used to form labeled conjugates which serve as the detection reagents in immunoassays for procainamide and NAPA.

The chemical structures of the drugs, with the $\alpha$- and $\beta$-positions on the amide side chain indicated, are represented by the formula:

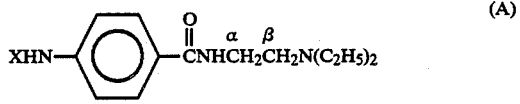

(A)

wherein X is hydrogen for procainamide and acetyl for NAPA. The synthesis of α-derivatives can be achieved by variations in the known synthesis of the parent drugs.

α-Derivatives

Figure 1:
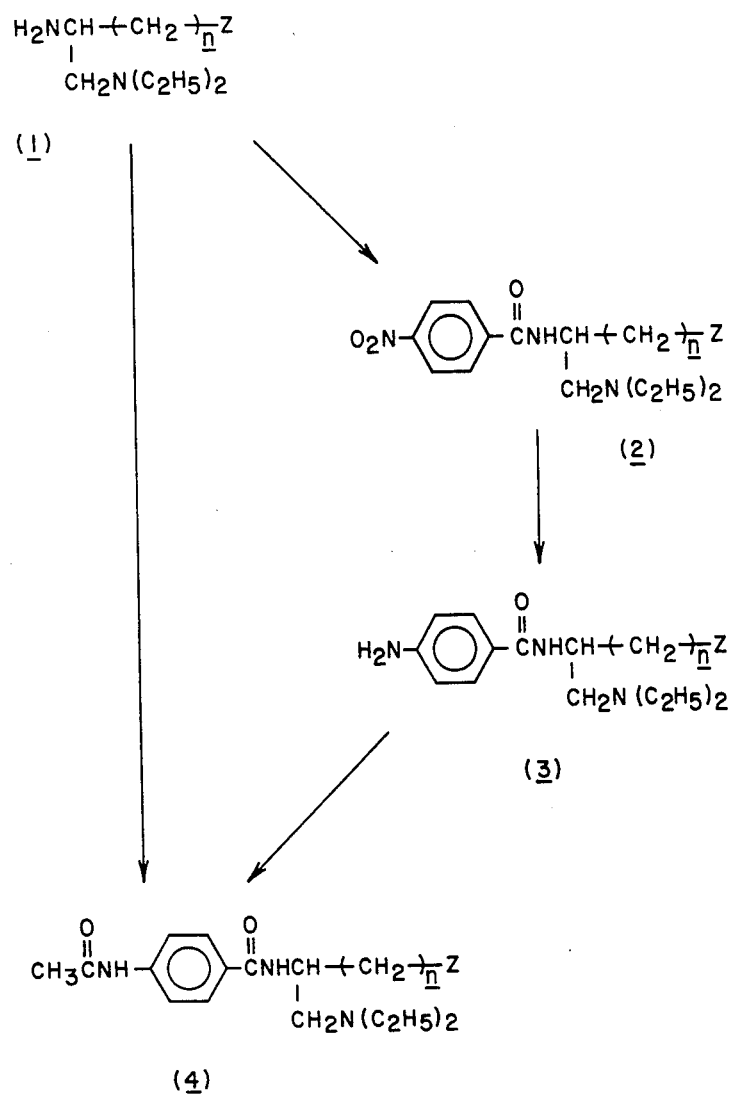
FIGS. 1 and 2 illustrate particular synthetic schemes for preparing $\alpha$-derivatives of procainamide and NAPA and for preparing a particularly useful intermediate for use in such derivatizations of the drugs.

With reference to FIG. 1 of the drawings, an appropriately functionalized (group designated Z) N,N-diethylethylenediamine derivative (1) is benzoylated by reaction with 4-nitrobenzoyl chloride to give nitro-substituted intermediates (2). Reduction of the nitro group produces the α-substituted procainamide derivatives (3) which upon acetylation yield the α-substituted NAPA derivatives (4) [M. Yamazohi, et al, *J. Pharm. Soc. Japan* 73: 294 (1953); R. Baltzly, et al, *J. Am. Chem. Soc.* 64: 2231 (1941); and D. E. Drayer et al, *Proc. Soc. Exp. Biol. Med.* 146: 358 (1974)]. Alternatively, the NAPA derivatives (4) can be produced directly from (1) by reaction with 4-acetamidobenzoic acid which has been activated with a carboxyl-activating reagent such as those used in amide bond-forming reactions [see "The Peptides", vol, 1, E. Gross and J. Meienhofer, eds., Academic Press (New York 1979) pp. 66 et seq].

Figure 2:
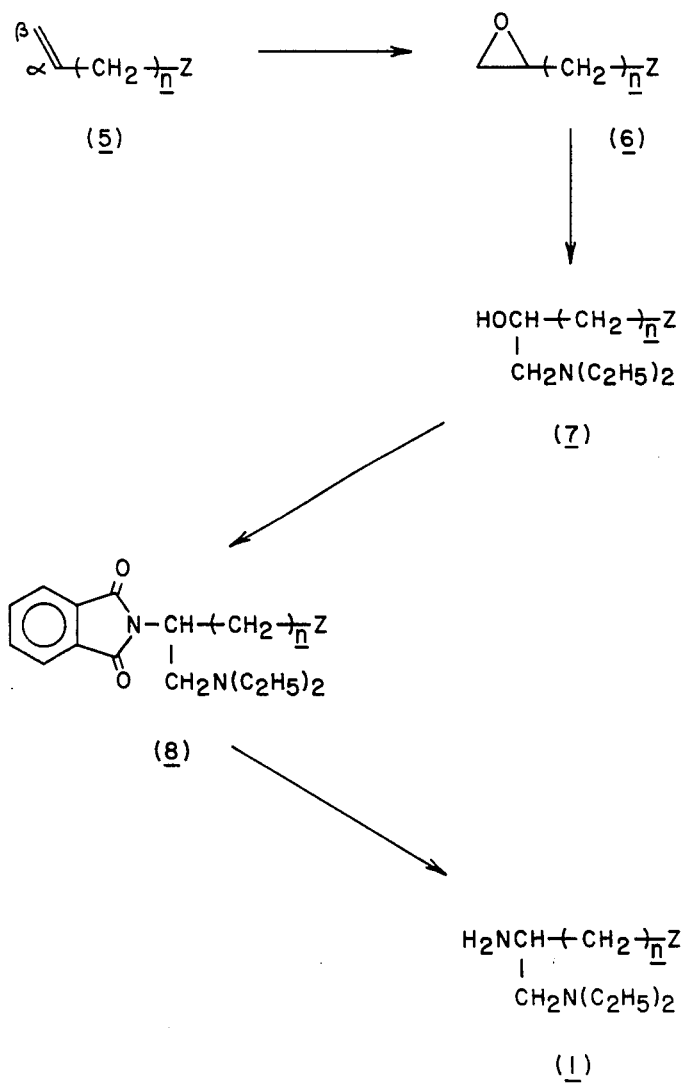

The key intermediate in the preparation of the α-substituted derivatives is the primary amine (1). The synthesis of this intermediate is outlined in FIG. 2 of the drawings beginning from the terminal olefin (5), n=1–10. The precursors to the α and β carbon atoms in procainamide and NAPA (A) are the carbon atoms of the double bond of (5). The double bond is epoxidized with 3-chloroperbenzoic acid to give oxiranes (6) which react with diethylamine to produce the amino alcohols (7). Reaction of (7) with phthalimide and diethyl azodicarboxylate leads to the phthalimido derivatives (8) which upon treatment with hydrazine gives the key primary amine reagent (1) [O. Mitsunobu, et al, *J. Am. Chem. Soc.* 94: 679 (1972)].

The resulting α-substituted procainamide and NAPA derivatives are of the formula:

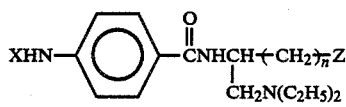

(B)

wherein X is as defined above, n is an integer from 1 through 10, preferably 1 through 6, and Z is a functional group capable of being coupled to immunogenic carrier materials or labeling reagents. Functional group Z is commonly amino, carboxyl, thiol, hydroxyl, or maleimido. Such α-functionalized derivatives are prepared from the appropriately functionalized olefins (5). For Z=hydroxyl, ω-hydroxy olefins are commercially available based on metal hydride reduction of the ω-olefinic esters [R. M. Scarborough, et al, *J. Am. Chem. Soc.* 102: 3904 (1980)] or by partial reduction of the corresponding ω-hydroxy acetylenes. For Z=amino, the corresponding ω-olefins can be obtained by reaction with phthalimide and diethyl azodicarboxylate followed by reaction with hydrazine [Mitsunobu supra]. Derivatives for Z=carboxyl are obtained from the corresponding ω-olefinic esters [Scarborough, supra].

Derivatives with Z=maleimido can be obtained by reacting α-aminated derivatives with N-succinimidyl m-maleimidobenzoate [T. Kitagawa, et al, *J. Biochem.* 79: 233 (1976)]. Finally, derivatives with Z=thio can be prepared by reaction of the primary amino derivative with SAMSA reagent [I. M. Klotz, et al, *Arch. Biochem. Biophys.* 95: 605 (1962)].

It will be evident to one of ordinary skill in the art that the above-described synthetic schemes, or simple modifications thereof, can be applied to the derivatization of other molecules, particularly drugs, which possess the same amide side chain as procainamide and NAPA without departing from the inventive concept presented herein. The resulting α-substituted derivatives can then of course be used to couple to carrier molecules or labeling reagents as will be described more fully below. Examples of such other molecules to which the present invention can be applied equivalently are metoclopramide [*Merck Index*, 9th ed. (1976) p. 801] and dibucaine [ibid, p. 399].

Immunogens

The above-described α-functionalized derivatives can be covalently linked by any number of conventional techniques to immunogenic carrier materials to yield immunogens comprising one or more residues of the formula:

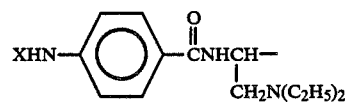

wherein X is as defined above.

More particularly such immunogens will have the formula:

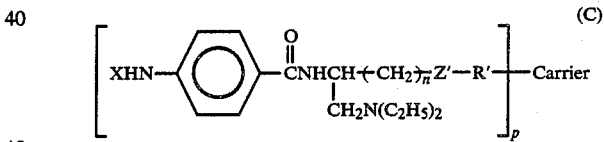

(C)

wherein n is defined above, Z' is the residue from functional group Z remaining after the coupling reaction, R' is a bond or an appropriate linking group, Carrier is an immunogenic carrier material, and ρ is the number of hapten moieties conjugated to the carrier. The number ρ is sometimes referred to as the epitopic density of the immunogen and is limited only by the number of available coupling sites on the carrier molecule. However, in the usual situation where the carrier is a protein such as albumin, ρ will be on the average from 1 to about 50, more normally from 1 to about 25. Optimal epitopic densities in such usual case, considering the ease and reproducibility of synthesis of the immunogen and antibody response, fall between about 2 and about 20, more usually between 5 and 15.

The immunogenic carrier material can be selected from any of those conventionally known. In most cases, the carrier will be a protein or polypeptide, although other materials such as carbohydrates, polysaccharides, lipopolysaccharides, nucleic acids and the like of sufficient size and immunogenicity can likewise be used. For the most part, immunogenic proteins and polypeptides will have molecular weights between 5,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins having significant nonproteinaceous constituents, e.g., glycoproteins, and the like. The albumins and globulins of molecular weight between 30,000 and 200,000 are particularly preferred. Further reference for the state-of-the-art concerning conventional immunogenic carrier materials and techniques for coupling haptens thereto may be had to the following: Parker, *Radioimmunoassay of Biologically Active Compounds,* Prentice-Hall (Englewood Cliffs, N.J. USA, 1976); Butler *J. Immunol. Meth.* 7: 1–24 (1975); Weinryb and Shroff, *Drug Metab. Rev.* 10: 271–283 (1975); Broughton and Strong, *Clin. Chem.* 22: 726–732 (1976); and Playfair et al, *Br. Med. Bull.* 30: 24–31 (1974).

Residue Z' will vary according to the functional group Z in α-derivative (B) used, and preferably will be imino, carboxyl, sulfo, or oxy.

Preferably, group R' is a bond to an appropriate functional group in the carrier material. Appropriate α-substituted drug derivatives are couplable to immunogenic carrier materials according to well known techniques. For example, the amino derivatives can be attached directly to the carrier by the following means. The amino group of the drug moiety can be attached to amino-containing carriers (e.g., protein or polypeptide carriers) by toluene-2,4-diisocyanate [A. F. Schick and S. J. Singer, *J. Biol. Chem.* 236: 2477 (1961)]; 4,4'-difluoro-3,3'-dinitrodiphenyl sulfone [P. S. Cuatrecasas, et al, *J. Biol. Chem.* 244: 406 (1969)]; glutaraldehyde [L. A. Frohman, et al, *Endocrinol.* 87: 1055 (1970)]; bis-imidates [A. Dutton, et al, *Biochem. Biophys. Res. Comm.* 23: 730 (1966)]; and chlorotriazine [T. Lang, et al, *J. C. S. Perkin* 4: 2189 (1977)]. Also, the amino derivatives can be coupled to carboxyl-bearing carriers (e.g., again, protein or polypeptide carriers) by common peptide bond-forming reactions by means of mixed anhydrides, activated esters, acyl azide formation, carbodiimides, etc., see *Peptides,* ed. Goodman and Meinhofer, John Wiley & Sons (New York, 1977) p, 6 et seq, and *The Peptides, Analysis, Synthesis, Biology,* Vol. 1, Academic Press (New York 1979). The same methods apply likewise for attaching carboxylated derivatives to amino-bearing carriers.

Thiolated derivatives can be attached to thiol-containing polymers (IgG or thiolated proteins) by the disulfide exchange procedure [J. Martin, et al, *Biochem.* 20: 4229 (1981)]. Alternately, an amino-containing polymer can be reacted with the reagent MBS and the product coupled to thiol-containing derivatives by the process described by T. Kitagawa and T. Aikawa, *J. Biochem.* 79: 233 (1976). Maleimide derivatives can similarly be coupled to thiol-containing carriers [ibid]. Hydroxy derivatives can be attached to carriers using trichlorotriazine [G. Kay and E. M. Crook, *Nature* 216: 514 (1967)].

A multitude of other coupling techniques are available to those of ordinary skill in the art for joining the various α-substituted derivatives of the present invention with conventional immunogenic carrier materials. For example, one skilled in the art can react an appropriate α-substituted derivative (B) with a Bifunctional reagent such that one end thereof covalently couples with the derivative and the other end has a functional group for coupling to carriers as described above (e.g., amino, carboxyl, thiol, hydroxyl, and maleimido). For example, bifunctional coupling reagents are well known for coupling amine derivatives to amino-containing macromolecules (e.g., proteins and polypeptides), including bis-imidates, bis-isocyanates, and glutaraldehyde [Immunochem. 6: 53 (1969)]. Other useful coupling reactions are thoroughly discussed in the literature [see Kopple, *Peptides and Amino Acids,* W. A. Benjamin, Inc. (New York 1966); Lowe and Dean, *Affinity Chromatography,* John Wiley & Sons (New York 1974); Means and Feeney, *Chemical Modification of Proteins,* Holden-Day (San Francisco 1971); and Glazer et al, *Chemical Modification of Proteins,* Elsevier (New York 1975)].

As a result, linking group R' and residue Z' can be considered as a single bridge group R, and thus the immunogens have the general formula:

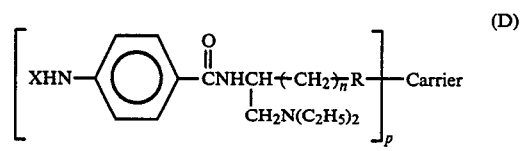
(D)

wherein R comprises the residue —Z'—R'— and may vary widely, its exact chemical structure not being critical so long as it serves the purpose of linking the hapten residue without interfering with the immunogenic properties of the resulting immunogen. For example, R can comprise linear or branched alkylene comprising from 1 to as many as 15, more usually 10 or less, and normally less than 6, carbon atoms (e.g., methylene, ethylene, n-propylene, iso-propylene, n-butylene, and so forth). In addition, such alkylene can contain other substituent groups such as cyano amino (including substituted amino), acylamino, halogen, thiol, hydroxyl, carbonyl groups, carboxyl (including substituted carboxyls such as esters, amides, and substituted amides). Bridge group R can also contain or consist of substituted or unsubstituted aryl, aralkyl, or heteroaryl groups (e.g., phenylene, phenethylene, and so forth). Additionally, such linkages can contain one or more heteroatoms selected from nitrogen, sulfur and oxygen in the form of ether, ester, amido, amino, thio ether, amidino, sulfone, or sulfoxide. Preferably R will be a chain, usually aliphatic comprising between 1 and about 20 atoms, more usually between 1 and 10, excluding hydrogen, of which between 0 and 5 are heteroatoms selected from nitrogen, oxygen, and sulfur. Accordingly, the choice of bridge group R is not critical to the present invention and may be varied widely by one of ordinary skill in the art.

Particularly preferred are the immunogens of the formula:

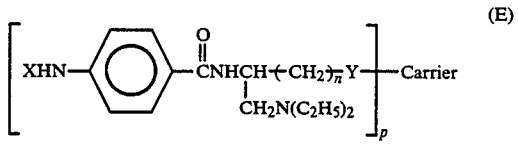
(E)

wherein X is as defined above, Y is an amide group, i.e., —NHCO—, Carrier is an immunogenic protein or polypeptide, n is an integer from 1 through 10, preferably from 1 through 6, and p is on the average from 1 to the number of available amide coupling sites on the carrier material and preferably is as defined above. The amide coupling group can be oriented in either of the two possible ways, with the nitrogen atom in the amide group being from carrier amino groups and the carbon atom being from an appropriate α-substituted derivative (e.g., a carboxylic acid), with p then representing the average number of coupled amino groups in the carrier (and preferably is as defined above), or with the nitrogen atom being from an appropriate α-substituted derivative (e.g., an amino derivative) and the carbon atom being from carrier carboxyl groups, with p then representing the average number of coupled carboxyl groups in the carrier (and preferably is again as defined above).

Antibodies

Preparation of specific antibodies using the present immunogen conjugates may follow any conventional technique. Numerous texts are available describing the fundamental aspects of inducing antibody formation, for example reference may be made to Parker, *Radioimmunoassay of Biologically Active Compounds*, Prentice-Hall (Englewood Cliffs, N.J. USA, 1976). In the usual case, a host animal such as a rabbit, goat, mouse, guinea pig, or horse is injected at one or more of a variety of sites with the immunogen conjugate, normally in mixture with an adjuvant. Further injections are made at the same site or different sites at regular or irregular intervals thereafter with bleedings being taken to assess antibody titer until it is determined that optimal titer has been reached. The host animal is bled to yield a suitable volume of specific antiserum. Where desirable, purification steps may be taken to remove undesired material such as nonspecific antibodies before the antiserum is considered suitable for use in performing actual assays.

The antibodies can also be obtained by somatic cell hybridization techniques, such antibodies being commonly referred to as monoclonal antibodies. Reviews of such monoclonal antibody techniques are found in *Lymphocyte Hybridomas*, ed. Melchers et al. Springer-Verlag (New York 1978), *Nature* 266: 495 (1977), *Science* 208: 692 (1980), and *Methods in Enzymology* 73 (Part B): 3–46 (1981).

Immunoassay Techniques

The antibodies prepared from the immunogens of the present invention can be used in any immunoassay method, and the corresponding reagent system, for determining procainamide and NAPA, including agglutination techniques, radioimmunoassays, heterogeneous enzyme immunoassays (cf. U.S. Pat. No. 3,654,090), heterogeneous fluorescent immunoassays (cf. U.S. Pat. Nos. 4,201,763; 4,171,311; 4,133,639 and 3,992,631), and homogeneous (separation-free) immunoassays. The latter-most are particularly preferred and include such techniques as fluorescence quenching or enhancement (cf. U.S. Pat. No. 4,160,016), fluorescence polarization (cf. *J. Exp. Med.* 122: 1029 (1965), enzyme substrate-labeled immunoassay (cf. U.S. Pat. No. 4,279,992 and U.K. Pat. Spec. No. 1,552,607), prosthetic group-labeled immunoassay (cf. U.S. Pat. No. 4,238,565), enzyme modulator-labeled immunoassay, e.g., using inhibitor labels (cf. U.S. Pat. Nos. 4,134,792 and 4,273,866), enzyme-labeled immunoassay (cf. U.S. Pat. No. 3,817,837), energy transfer immunoassay (cf. U.S. Pat. No. 3,996,345), and double antibody steric hindrance immunoassay (cf. U.S. Pat. Nos. 3,935,074 and 3,998,943). Homogeneous immunoassays are typically performed by setting up competition between the analyte and the labeled conjugate of the drug for binding to antibody and are characterized by the fact that the detectable label property is altered when the labeled conjugate is bound by antibody.

Moreover, the α-substituted derivatives of the present invention can be used to prepare the labeled conjugates needed to perform the various immunoassays described above. Appropriate derivatives can be radiolabeled or labeled with fluorescent moieties in accordance with standard methods. Likewise the appropriate labeling moiety for the preferred homogeneous techniques, e.g., an enzyme substrate, a prosthetic group, an enzyme modulator, or an enzyme (which is a protein and can be coupled similarly to the immunogenic carrier as described above) can be coupled to the α-substituted derivatives to yield labeled conjugates.

Particularly preferred labeled conjugates are the β-galactosyl-umbelliferone-procainamide/NAPA conjugates of the formula:

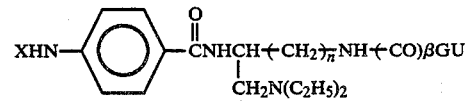

wherein —CO)βGU is

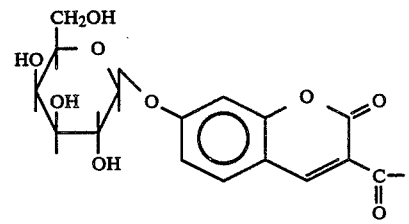

and n is an integer from 1 through 10. Such conjugates are prepared by standard peptide condensations of β-galactosyl-umbelliferone carboxylic acid (U.S. Pat. No. 4,226,978) with the appropriate α-amino derivative.

The reagent system or means of the present invention comprises all of the essential chemical elements required to conduct a desired procainamide or NAPA immunoassay method encompassed by the present invention. The reagent system is presented in a commercially packaged form, as a composition or admixture where the compatibility of the reagents will allow, in a test device configuration, or as a test kit, i.e., a packaged combination of one or more containers holding the necessary reagents. Included in the reagent system are the reagents appropriate for the binding reaction system desired, e.g., an antibody and labeled conjugate of the present invention. Of course, the reagent system can include other materials as are known in the art and which may be desirable from a commercial and user standpoint, such as buffers, diluents, standards, and so forth. Particularly preferred is a test kit for the homogeneous competitive binding immunoassay of the present invention comprising (a) an antibody of the present invention and (b) a labeled conjugate which has a detectable property which is altered when bound with the antibody. Also preferred is a test device comprising a reagent composition including an antibody of the present invention and a labeled conjugate which has a detectable property which is altered when bound with the antibody, and a solid carrier member incorporated with the reagent composition. The various forms of such test device are described in U.S. Pat. Appln. Ser. No. 202,378, filed Oct. 30, 1980, which is incorporated herein by reference and which has published as European patent application No. 51,213. The specific label used in the preferred test kit and test device will depend on the technique followed, as described hereinabove.

The present invention will now be illustrated, but is not intended to be limited, by the following examples:

EXAMPLES

Reagents

Italicized numbers appearing after chemical names refer to the structural formulae identified in the text above and/or in the drawings.

A. Preparation of drug derivative

N-(1-Hexen-6-yl)phthalimide, (5), Z=phthalimido, n=4.

To a stirred solution of 1-hexene-6-ol [R. E. Lyle, et al, *J. Org. Chem.* 21: 61 (1956) in 1 liter (L) of ether containing 40.5 grams (g) [0.4 moles)(mol)] of triethylamine was added dropwise a solution of 45.8 g (0.4 mol) of methanesulfonyl chloride in 100 milliliters (mL) of ether. After 3 hours at room temperature, the mixture was filtered and evaporated to give an oil. It was combined with 600 mL of dry dimethyl formamide (DMF) and 75 g (0.4 mol) of potassium phthalimide and heated at 100° C. for 12 hours. The solvent was removed under vacuum and the residue partitioned between ethyl acetate and $H_2O$. The organic phase was dried over anhydrous magnesium sulfate ($MgSO_4$), filtered, and evaporated to leave 80 g of an oily solid. It was taken up in hexane, filtered, and the filtrate fractionally distilled to give 65 g (75% yield) of N-(1-hexen-6-yl) phthalimide as a clear oil, boiling point (bp) 128°–135° C. (0.01 torr).

N-(5-Epoxyhexyl)phthalimide, (6), Z=phthalimido, n=4.

A solution of 2.3 g [10 millimoles (mmol)] of the above phthalimide in 50 mL of methylene chloride ($CH_2Cl_2$) was stirred with 1.29 g (15 mmol) of sodium bicarbonate ($NaHCO_3$) while a solution of 2.6 g (15 mmol) of 3-chloroperbenzoic acid in 25 mL of $CH_2Cl_2$ was added. After stirring for 3 hours at room temperature, excess peracid was destroyed by the addition of 20 mL of 10% sodium sulfite ($Na_2SO_3$) solution. The organic phase was separated, washed with saturated $NaHCO_3$ solution, washed with saturated sodium chloride (NaCl) solution, then dried over anhydrous $MgSO_4$. It was filtered and evaporated leaving a residue which was fractionally distilled to give 1.6 g (64% yield) of the epoxide as an oil, bp 156°–160° C. (0.01 torr).

Analysis: Calculated for $C_{14}H_{15}NO_3$: C, 68.55; H, 6.16; N, 5.71. Found: C, 68.83; H, 6.27; N, 5.70.

N-(6-Diethylamino-5-hydroxyhexyl)phthalimide, (7), Z=phthalimido, n=4.

A mixture of 24.5 g (0.1 mol) of the preceeding epoxide, 22 g (0.3 mol) of diethylamine, and 50 mL of ethanol was heated at 100° C. in a steel autoclave for 7 hours. When cool, the autoclave was opened and the contents removed and evaporated under reduced pressure. The residue was partitioned between ether and 10% hydrochloric acid. The aqueous phase was separated, made basic with sodium hydroxide (NaOH) solution, and extracted with ether. Removal of the ether left an oily redisue which was fractionally distilled to give 13.6 g (43% yield) of the phthalimide as a clear oil, bp 180°–185° C. (0.1 torr).

Analysis: Calculated for $C_{18}H_{26}N_2O_3$: C, 67,89; H, 8.23; N, 8.80. Found: C, 68.09; H, 8.30; N, 9.42.

6-Amino-1-diethylamino-2-hydroxyhexane, (7), Z=amino, n=4.

The preceeding phthalimide (9.21 g, 29 mmol) was dissolved in 150 mL of methanol containing 1.8 g (36 mmol) of hydrazine hydrate and refluxed for 3 hours. The reaction was cooled, filtered, and the filtrate fractionally distilled to give 4.24 g (78% yield) of the diamine as a clear oil, bp 92°–96° C. (0.01 torr).

Analysis: Calculated for $C_{10}H_{24}N_2O$: C, 63.78; H, 12.85; N, 14,88. Found: C, 63.57; H, 12.34; N, 14.15.

6-(tert-Butyloxycarbonylamino)-1-diethylamino-2-(N-phthalimido)hexane, (8), Z=protected amino, n=4.

A mixture of 4 g (21 mmol) of the preceeding diamine, 4.6 g (21 mmol) of di-tert-butyl dicarbonate, and 100 mL of dry $CH_2Cl_2$ was stirred for 12 hours at room temperature. Solvent and volatile by-products were removed by evaporation under reduced pressure, leaving 6 g (100% yield) of 6-(tert-butyloxycarbonylamino)-1-diethylamino-2-hydroxyhexane as an oil which was not further purified. It was dissolved in 100 mL of dry tetrahydrofuran (THF) along with 3.27 g (22 mmol) of phthalimide, 5.77 g (22 mmol) of triphenylphosphine, and 3.83 g (22 mmol) of diethyl azodicarboxylate (DEAD). The solution was stirred at room temperature for 12 hours at which point, to complete the reaction, an additional 1.64 g (11 mmol) of phthalimide and 1.92 g (11 mmol) of DEAD were added and stirring continued for 1 hour. Solvent was removed and the residual oil partitioned between ether and 1% hydrochloric acid. The aqueous phase was separated, made basic with NaOH solution, and extracted with ether. The ether extract was dried over anhydrous $MgSO_4$, filtered evaporated. A pale yellow oil resulted which was dried under high vacuum to afford 9.2 g of the protected amino-phthalimide as a pale yellow oil.

N-[1-(4-tert-Butyloxycarbonylaminobutyl)-2-(diethylamino)ethyl]-4-nitrobenzamide, (2), Z=protected amino, n=4.

The preceeding oil was converted to the free amine [(1), Z=amino, n=4] by refluxing it for 2 hours in 200 mL of ethanol containing 1.2 g (24 mmol) of hydrazine hydrate. The solution was cooled, filtered, and the solvent removed under reduced pressure to give an oil which was partitioned between ether and 10% NaOH solution. The organic phase was separated, washed with $H_2O$, saturated NaCl solution, and dried over anhydrous $MgSO_4$. Filtration and evaporation of the filtrate gave 5.53 g of the primary amine as a clear oil. This solution was dissolved in 200 mL of dry THF. To the solution was added 20 g of anhydrous $K_2CO_3$ and 7.14 g (38 mmol) of 4-nitrobenzoyl chloride. After stirring for 12 hours at room temperature, solvent was removed under reduced pressure, and the residue partitioned between ether and 10% NaOH solution. The organic phase was separated, washed with additional 10% NaOH solution, then extracted with 1% hydrochloric acid. The aqueous acid phase was separated, made basic with NaOH, and extracted with ether. The ether phase was dried over anhydrous $MgSO_4$, filtered, and evaporated. The oily residue was crystallized from ether to give 4.6 g of the nitrobenzamide as a solid, mp 109°–111° C.

Analysis: Calculated for $C_{22}H_{36}N_4O_5$: C, 60,53; H, 8.31; N, 12.84. Found: C, 60.50; H, 8.44; N, 12.56.

N-[1-(4-Aminobutyl)-2-(diethylamino)ethyl]-4-aminobenzamide, (3), Z=amino, n=4.

A solution of 4.5 g (10 mmol) of the preceeding nitrobenzamide in 100 mL of ethanol was hydrogenated at 50 pounds per square inch hydrogen (psi $H_2$) over 500 mg of 10% Paladium on carbon (Pd/C). It was filtered and evaporated to give 3.45 g of the aromatic amine as an oil. This was dissolved in 50 mL of anhydrous trifluoroacetic acid and allowed to stand 1 hour at 0° C. Excess trifluoroacetic acid was removed under reduced pressure and the residue was taken up in $H_2O$. It was filtered and the filtrate saturated with KCl, and made basic with NaOH. The solution was extracted with $CHCl_3$ and the extract dried, filtered, and evaporated. This left 1.4 g of the amino-functionalized procainamide derivative (3), $Z=NH_2$, n=4 as a clear oil.

B. Preparation of immunogen

The amino-functionalized procainamide derivative prepared above [9.5 mg (35 μmol)] was dissolved in 0.5 mL of distilled water in a test tube. A small magnetic stir bar was added and the pH of the solution was adjusted to pH 4.0 with 0.1 normal (N) HCl. The solution was cooled in an ice bath and 9.6 milligrams (50 μmoles) of 1-ethyl-3-(3-dimethylaminopropyl)carbodiimide was added and dissolved. Bovine serum albumin (25 mg, 35 μmoles) dissolved in 0.5 mL of distilled $H_2O$ was slowly added to the solution containing the procainamide derivative and carbodiimide. The reaction incubated for 24 hours at 4° C., and then was dialyzed against one liter of distilled water which was changed three times. Sodium azide was added to a final concentration of 0.1%. The protein concentration of the immunogen was adjusted to a concentration of 1 mg/mL with saline (0.85% NaCl).

Six milliliters of immunogen (1 mg/mL) was combined with 12 mL of Fruends Complete Adjuvant and 6 mL of saline. Rabbits were immunized simultaneously each with 2 mL of this mixture. Four weeks later they were reimmunized with the same mixture prepared with incomplete Fruends adjuvant. The booster immunizations were repeated every two weeks. Test bleedings were taken one week after the boosters. Antiserum with suitable titers were obtained by four months after the initial immunization.

C. Preparation of labeled conjugate
N-[4-(4-Aminobenzamido)-4-(2-diethylaminoethyl)-butyl]-7-β-galactosylcoumarin-3-carboxamide.

To a stirred suspension of 1.4 g (3.8 mmol) of 7-β-galactosylcoumarin-3-carboxylic acid [J. F. Burd, et al, Clin. Chem. 23: 1402 (1977)] in 40 mL of dry DMF was added 400 mg (4 mmol) triethylamine. The mixture was stirred until homogeneous, cooled to −10° C. under argon, and combined with 510 mg (4 mmol) of isobutyl chloroformate. The reaction was stirred at this temperature for 30 minutes to complete the formation of the mixed anhydride. A solution of the preceeding diamine, (3), Z=amino, n=4 [1.15 g, 3.8 mmol] in 25 mL of DMF was added and the reaction allowed to stand at 0° C. for 12 hours. Concentration on a rotary evaporator attached to a vacuum pump left a glassy residue which was taken up in $H_2O$ and filtered. The pH of the filtrate was adjusted to 8.0 with $NaHCO_3$ solution, 20 g of silica gel was added, and the solvent removed under reduced pressure. The impregnated adsorbent was placed atop a column of 100 g of silica gel made up in ethyl acetate. The column was washed with 1 liter of ethyl acetate (discarded), then eluted with ethanol. Twenty mL fractions were collected. Fractions 50–221 were pooled and evaporated to give 330 mg (13% yield) of the labeled procainamide conjugate as a white solid, mp 175°–177° C.

Immunoassay Method

A homogeneous substrate-labeled fluorescent immunoassay (SLFIA—U.S. Pat. No. 4,279,992) for procainamide was established as follows:

A. Reagents
1. Antibody/Enzyme Reagent—50 mM Bicine buffer [N,N-bis-(2-hydroxyethyl)glycine], (Calbiochem-Behring Corp., LaJolla, CA), pH 8.3, containing 0.0015 units/mL β-galactosidase, sufficient antiserum raised against the procainamide immunogen to decrease fluorescence to 22% of that in the absence of antiserum and 15.4 nM sodium azide.
2. Conjugate Reagent—30 mM formate buffer, pH 3.5, containing 0.01% (v/v) Tween 20 detergent (Fisher Scientific, Fairlawn, NJ, USA) and 0.020 $A_{343}$ units of β-GU-procainamide.
3. Procainamide Standards—USP reference standard procainamide added to normal human serum; diluted 51-fold with 50 mM Bicine buffer, containing 15.4 mM sodium azide.

B. Inhibition of Hydrolysis of β-GU-Procainamide by Antiserum to Procainamide

Increasing amounts of antiserum were added to 1.5 mL of Bicine buffer containing 0.0015 units/mL β-galactosidase. The reaction was initiated with 50 μL of the Conjugate Reagent added to each cuvette with mixing. After twenty minutes the fluorescence intensity was measured in each cuvette (excitation 400 nm, emission 450 nm). The results are presented in Table 1.

TABLE 1

| μL Antiserum | Fluorescence |
|---|---|
| 0 | 2.7 |
| 4 | 2.3 |
| 8 | 0.6 |
| 12 | 0.4 |
| 15 | 0.3 |

C. Assay Method and Results

To 1.5 mL of the Antibody/Enzyme Reagent in cuvettes was added 50 μL (microliters) of the diluted procainamide standards. Then to begin the reaction, 50 μL of the Conjugate Reagent was added to each cuvette with mixing. After 20 minutes the fluorescence intensity was measured in each cuvette (excitation 400 nm, emission 450 nm).

Performance of the assay yielded the results shown in Table 2.

TABLE 2

| Procainamide (μg/mL) | Fluorescence |
|---|---|
| 0 | 3.2 |
| 4 | 5.1 |
| 8 | 7.0 |
| 12 | 8.6 |
| 16 | 9.7 |

The immunoassay could be used to determine procainamide concentrations in serum samples.

What is claimed is:
1. A compound of the formula:

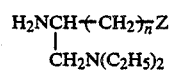

wherein n is an integer from 1 through 6 and Z is carboxyl or amino.
2. The compound of claim 1 wherein Z is amino.
3. The compound of claim 2 wherein n=4.